United States Patent [19]

Swallert

[11] Patent Number: 4,850,979
[45] Date of Patent: Jul. 25, 1989

[54] HOLDING AND HANDLING DEVICE OF A SYRINGE

[75] Inventor: Sven A. Swallert, Geneva, Switzerland

[73] Assignee: Cameco Medical Limited, London, England

[21] Appl. No.: 146,130

[22] Filed: Jan. 20, 1988

[30] Foreign Application Priority Data

Feb. 11, 1987 [CH] Switzerland ............ 511/87

[51] Int. Cl.⁴ .......................................... A61M 5/315
[52] U.S. Cl. .................................................. 604/228
[58] Field of Search ............... 604/227, 228, 223, 187, 604/136, 135, 134

[56] References Cited

U.S. PATENT DOCUMENTS 3,819,091  6/1974  Hollender ........................... 604/223
4,594,073  6/1986  Stine .
4,711,250 12/1987  Gilbaugh, Jr. et al. ............ 604/228

FOREIGN PATENT DOCUMENTS 1054316  2/1954  France ............................... 604/136
2142827  1/1985  United Kingdom .

Primary Examiner—John D. Yasko
Attorney, Agent, or Firm—Young & Thompson

[57] ABSTRACT

The invention relates to a holding and handling device of a syringe, which comprises a handle (1), a holding portion (2), two parallel guiding rods (3) rigidly linking the handle and the holding portion, and a gripping member (10) slidably axially mounted between both guiding rods and turning on itself around its central axia. A fixing plate (7) having a central opening is displaceably mounted parallel to the upper surface of the supporting plate (4) and is subjected to the action of springs (8) leading to maintain this fixing plate into contact with said supporting plate, in such a manner that in service position the peripheral edge (13') of the cylindrical body (13) of the syringe is maintained by jamming between the fixing plate and the supporting plate. Finally, the gripping member presents coupling openings (11, 11') cooperating in service position with the upper end (14') of the piston (14) of the syringe.

10 Claims, 2 Drawing Sheets

HOLDING AND HANDLING DEVICE OF A SYRINGE

The present invention is concerning a holding and handling device of a syringe.

It is known to use syringes of the usual type for practicing biopsies by aspiration, with a view to a diagnosis examination of a determined substance taken from the body of a living being. This technic is especially used for lumbar, prostatic, amnionic punctures, for the examination of tumors, etc. According to the nature and the consistency of the substance to be taken, the removal motion of the piston of the syringe necessitates more or less power. Furthermore, the free end of the piston of the syringe does not provide appropriate means for exercising this force in a manner as axial as possible. This is why, it turns out useful, even necessary, to have means available which allow the user to activate in a more precise manner the piston of the syringe.

The purpose of this invention thus consists in providing a holding and handling device of a syringe, which offers the above possibilities, and which can be used with syringes of different sizes.

The holding and handling device of a syringe according to the invention, which leads to reach the precited purpose, presents the features mentioned in claim 1.

The annexed drawing illustrates schematically and by way of example one embodiment of the device according to the invention.

Figure 1:
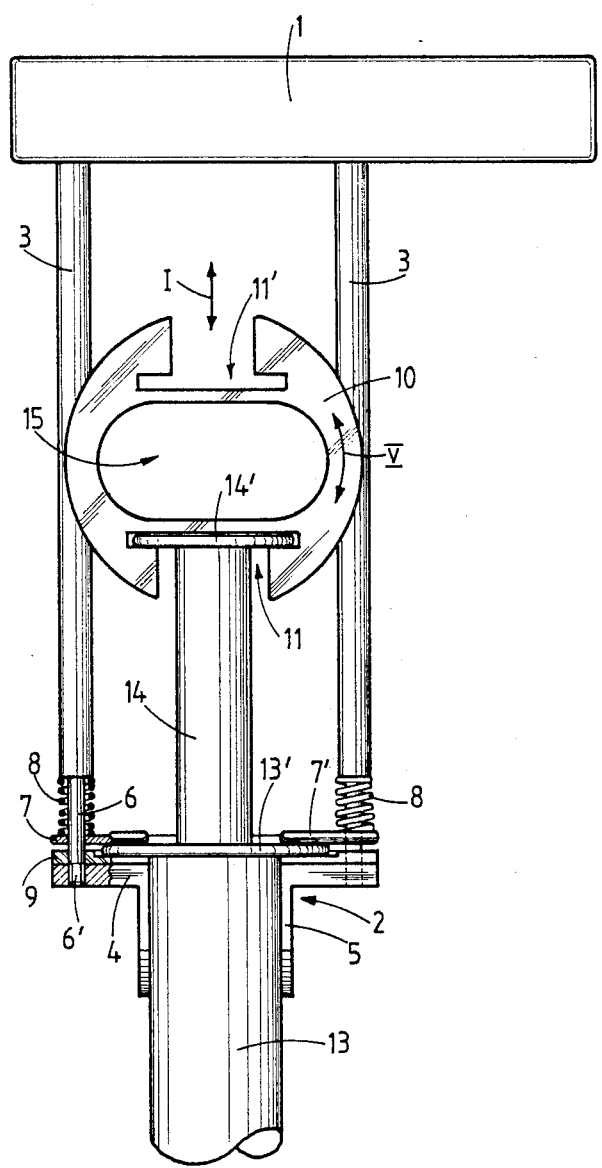
FIG. 1 is a face view thereof, partly sectional, with a syringe in service position.

By reference to the annexed drawing, the device according to the invention as shown comprises a handle 1, a holding portion 2 and two parallel guiding rods 3 rigidly linking the handle and the holding portion. This latter comprises a base plate 4 having a central opening and extended downwards by a partly cylindrical positioning skirt 5.

The lower parts 6 of the guiding rods 3 are presenting a smaller diameter than the remaining parts of the rods and threads 6' at their end, and are screwed in tappings made within the base plate 4 of the holding portion 2.

Furthermore, a fixing plate 7 is axially slidably mounted between both guiding rods 3, more particularly on the lower parts 6 thereof, and is subjected to the action of springs 8 mounted on these lower parts 6 and leading to maintain the fixing plate 7 against the upper face of the base plate 4 of the holding portion 2. This base plate 4 may further be provided on said upper face with a supporting plate 9, preferably made of a semi-rigid material.

Finally, the device comprises a gripping member 10 mounted between both guiding rods 3 in order to be freely axially displaceable by sliding on said rods (arrow I) and freely pivoting on itself around its central axis between these latters (arrow II). This gripping member is of a general circular shape, with two radial openings 11,11' of different sizes and diametrically opposed and presenting transverse notches. Between these radial openings 11,11', the gripping member 10 comprises on its peripheral edge two guiding grooves 12 intended to cooperate with the guiding rods 3 to allow these movements respectively of axial translation (I) and of rotation (II) as described above.

Figure 2:
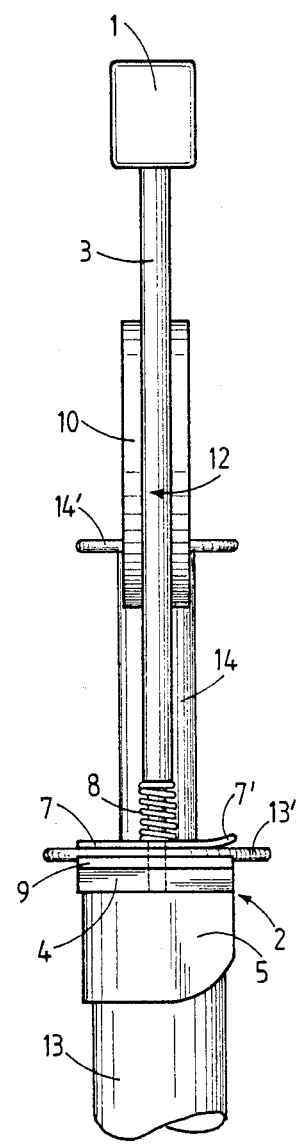
FIG. 2 is a side view thereof.

As illustrated on FIG. 1, a syringe 13 may be fixed in service position, by wedging the peripheral edge 13' located at the upper end of the cylindrical body of the syringe between the fixing plate 7 and the supporting plate 9, thanks to the action of the spring 8. In order to facilitate the introduction of said edge 13' between the fixing plate 7 and the supporting plate 9, the front edge 7' of the fixing plate is slightly lifted (see FIG. 2). With regards to the upper part of the cylindrical body the syringe 13, it is located in this service position within the cylindrical portion of the positioning skirt 5.

In the service position as shown, the free end of the piston 14 of the syringe 13 is maintained by a peripheral edge 14' in the notch 11 of the gripping member provided therefor.

The user has thus to hold the handle 1 with only one hand and simultaneously with two fingers, for example, introduced within the central opening 15 of the gripping member 10, to draw this one towards said handle 1, so as to cause by the removal of the piston 14 an aspiration in the cylindrical body of the syringe 13. Generally the lower end of the syringe 13 is directly provided with a hollow needle (not shown) or bound through a pipe to such a hollow needle, this latter being introduced into a particular zone of the living body from which the user intends to take a substance to be analyzed in the view to establish a diagnosis for example.

Figure 3:
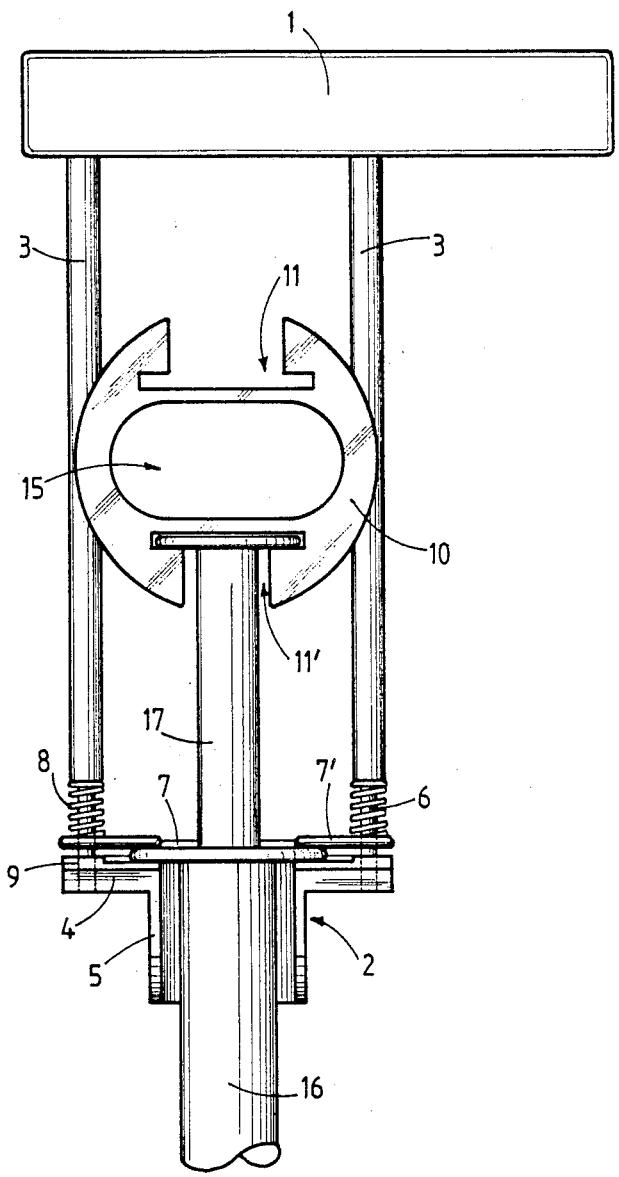
FIG. 3 is a face view thereof, also with a syringe in service position.

As shown on FIG. 3, the realization of the device according to the invention allows the use of syringes of different sizes. Thanks to the presence of the fixing plate 7, a syringe 16 of sizes smaller than those of the syringe 13 of FIG. 1 can be fixed without problem in service position in the positioning skirt 5, whose diameter of the cylindrical portion is clearly higher than that of the cylindrical body of this syringe 16. Furthermore, in this realization, the peripheral edge of the end of the piston 17 is located into the notch 11' of the gripping member 10 which is of different size.

The main advantages of the device according to the invention are consisting in the fact that it allows a precise handling of the piston of the syringe on one part, and that it is usable with types of syringes having different sizes.

I claim:

1. An apparatus for the holding and handling of a syringe, said apparatus comprising
    a handle,
    means to hold an outer body of a syringe in position, said means including a collar member surrounding a portion of said outer body of the syringe, and bias means to maintain an end shoulder portion of said outer body of said syringe fixed in position against an end portion of said collar member,
    two parallel guide rods extending between said handle and said collar member,
    finger gripping means positioned between said two parallel guide rods, said gripping means including a peripheral grooved portion, with said gripping means being slidably mounted between said parallel guide rods by engagement of said guide rods within a portion of said peripheral grooved portion,
    and said finger gripping means including means to releasably engage an end portion of the piston tube of syringes of at least two different sizes.

2. The apparatus of claim 1 wherein said finger gripping means includes an opening adapted for insertion of one or more fingers.

3. The apparatus of claim 1 wherein said finger gripping means is substantially circular in configuration.

4. The apparatus of claim 1 wherein said bias means comprises spring means mounted on portions of said parallel guide rods adjacent said end of said collar member.

5. The apparatus of claim 4 further including a positioning plate which is urged against said end shoulder portion of said outer body of said syringe by said spring means, said end shoulder portion being fixed in position between said plate and said end portion of said collar member by action of said spring means.

6. The apparatus of claim 5 wherein said positioning plate is slidably mounted on said parallel guide rods.

7. The apparatus of claim 5 wherein said positioning plate includes an upwardly extending edge portion which permits said positioning plate to be gripped by the fingers.

8. The apparatus of claim 1 wherein said collar member includes a layer of semi-rigid material against which said end shoulder portion is fixed in position.

9. The apparatus of claim 1 wherein said finger gripping means includes at least two cut-out portions each including a radial slot of a different size adapted to releasably receive an end portion of the piston tube of said syringe.

10. The apparatus of claim 1 wherein said gripping means is rotatably mounted between said parallel guide rods.

* * * * *